(12) United States Patent
Reymond et al.

(10) Patent No.: US 9,005,627 B2
(45) Date of Patent: Apr. 14, 2015

(54) CONTIGUOUS OVERLAPPING PEPTIDES FOR TREATMENT OF RAGWEED POLLEN ALLERGY

(75) Inventors: Christophe Reymond, Prilly (CH); Francois Spertini, Epalinges (CH)

(73) Assignee: Anergis S.A., Epalinges (CH)

( * ) Notice: Subject to any disclaimer, the term of this patent is extended or adjusted under 35 U.S.C. 154(b) by 0 days.

(21) Appl. No.: 13/533,656

(22) Filed: Jun. 26, 2012

(65) Prior Publication Data
US 2013/0004527 A1 Jan. 3, 2013

Related U.S. Application Data

(60) Provisional application No. 61/501,690, filed on Jun. 27, 2011.

(51) Int. Cl.
| | | |
|---|---|---|
| A61K 38/00 | (2006.01) | |
| A61K 38/04 | (2006.01) | |
| A61K 39/00 | (2006.01) | |
| A61K 39/35 | (2006.01) | |
| A61K 39/36 | (2006.01) | |
| A61K 39/38 | (2006.01) | |
| C07K 14/415 | (2006.01) | |

(52) U.S. Cl.
CPC ............... C07K 14/415 (2013.01); A61K 39/36 (2013.01)

(58) Field of Classification Search
None
See application file for complete search history.

(56) References Cited

U.S. PATENT DOCUMENTS

| 7,923,209 | B2 | 4/2011 | Spertini et al. |
| 2009/0324501 | A1 * | 12/2009 | Valenta et al. .................. 424/9.2 |
| 2010/0203070 | A1 | 8/2010 | Reymond et al. |

FOREIGN PATENT DOCUMENTS

| WO | WO 93/21321 | * | 10/1993 | ............. C12N 15/29 |
| WO | WO-9613589 A1 | | 5/1996 | |
| WO | WO-2004/081028 A2 | | 9/2004 | |
| WO | WO-2010089671 A2 | | 8/2010 | |

OTHER PUBLICATIONS

Bousquet et al., "Assessment of quality of life in patients with perennial allergic rhinitis with the French version of teh SF-36 Health Status Questionnaire," *J. Allergy Clin. Immunol*, 94(2):182-188 (1994).
Campbell et al., *J. Exp. Med.*, 206(7):1535-47 (2009).
Creticos et al., *N. Engl. J. Med.*, 355:1445-55 (2006).
Dam Petersen et al., "Clinical and patient based evaluation of immunotherapy for grass pollen and mite allergy," *Allergol et Immunopathol*, 33(5):264-269 (2005).
Drachenberg et al., "Single-course specific immunotherapy with mixed pollen allergoids: results of a multi-centre study," *Allergol et Immunopathol*, 31(2):77-82 (2003).
Fellrath et al., "Allergen-specific T-cell tolerance induction with allergen-derived long synthetic peptides: Results of a phase I trial," *J. Allergy Clin. Immunol*, 111(4):854-861 (2003).
Jahn-Schmid et al., *J. Allergy Clin. Immunol.*, 126(5):1068-1071 (2010).
Niederberger et al., "Vaccination with genetically engineered allergens prevents progression of allergic disease," *PNAS*, 101(2):14677-14682 (2004).
Pauli et al., "Efficacy of recombinant birch pollen vaccine for the treatment of birch-allergic rhinoconjunctivitis," *J. Allergy Clin. Immunol*, 122(5):951-60 (2008).
Purohit et al., "Clinical effects of immunotherapy with genetically modified recombinant birch pollen Bet v 1 derivatives," *Clinical and Experimental Allergy*, 38:1514-1525 (2008).
Settipane et al., "Demographics and Epidemiology of Allergic and Nonallergic Rhinitis," *Allergy and Asthma Proc.*, 22(4):185-189 (2001).
Wopfner, *IAAI*, 138(4):337-346 (2005).
Spertini et al., "Allergen-specific Immunotherapy of Allergy and Asthma: current and future trends," *Expert Rev. Resp. Med.*, 3(1): 37-51 (2009).
Anonymous, "Anergis Reaches Important Milestones with Second Product Candidate AllerR," XP055052380, Retrieved from the Internet: URL:http:..www.anergis.ch/uploads/tx_anergisnews/120614_Anergis_Reaches_Important_Milestones_with_Second_Product_Candidate_AllerR.pdf 9 [retrieved on Feb. 5, 2013].
Wopfner et al., "The alpha and beta subchain of Amb a 1, the major ragweed-pollen allergen show divergent reactivity at the IgE and T-cell level," *Molecular Immunology*, 46: 2090-2097 (2009).
Jahn-Schmid et al., "Humoral and Cellular Cross-Reactivity between Amb a 1, the Major Ragweed Pollen Allergen, and Its Mugwort Homolog Art v 6," J. Immunol, 188: 1559-1567 (2012).
International Search Report corresponding in PCT/IB2012/001545 mailed May 15, 2013.
Written Opinion in corresponding PCT/IB2012/001545 mailed May 15, 2013.
International Preliminary Report on Patentability in corresponding PCT/IB2012/001545 mailed Jan. 16, 2014.

* cited by examiner

*Primary Examiner* — Nora Rooney
(74) *Attorney, Agent, or Firm* — Marshall, Gerstein & Borun LLP

(57) ABSTRACT

Contiguous overlapping peptides (COPs) for the treatment of allergic patients by Specific Immunotherapy (SIT) are provided from the sequence of the major allergen of ragweed pollen Amb a 1. Such peptides while providing all potential T cell epitopes are devoid of the three-dimensional structure of the original allergen, therefore reducing their ability to bind IgE.

39 Claims, 4 Drawing Sheets

CONTIGUOUS OVERLAPPING PEPTIDES FOR TREATMENT OF RAGWEED POLLEN ALLERGY

CROSS-REFERENCE TO RELATED APPLICATIONS

This application claims priority benefit of U.S. Provisional Application 61/501,690 filed Jun. 27, 2011 the disclosure of which is incorporated herein by reference.

FIELD OF THE INVENTION

The present invention relates to contiguous overlapping peptides (COPs) derived from the Amb a 1 ragweed pollen major allergen and the use of such compounds in medicine. The compounds and methods of treatment of the invention are contemplated to be useful in treating ragweed pollen allergy and widely accelerating its treatment.

BACKGROUND OF THE INVENTION

IgE.mediated allergic disease appears to be very common particularly in industrialized countries where up to one quarter of the population is affected by allergic rhinitis. (Settipane, R. A., Allergy Asthma Proc, 22(4):185-9 (2001)). Furthermore people suffering from allergic rhinitis show a lower quality of life than healthy one, (Bousquet, J., et al., J Allergy Clin Immunol, 94(2):182-8 (1994)) with only a few going into remission spontaneously.

Ragweed (*Ambrosia artemisiifolia*) belongs to the Asteraceae plant family and represents the most important allergenic source within this genus. The *Ambrosia* sp. are native to eastern and central North America, but are also persistently spreading in Central and Southern Europe. The population allergic to ragweed pollen is increasing particularly in the US (Gadermaier, Allergy, 63(11): 1543-9 (2008)). In northern America, 45% of allergic individuals suffer from ragweed pollen allergy. In Europe, atopic sensitization in ragweed-populated areas (e.g. France, Italy, Austria, Hungary, Croatia and Bulgaria) is constantly increasing.

A few allergen proteins have been associated with ragweed allergy. Sequences of such ragweed allergens (Amb a) can be found in the Nucleotide protein databases (NCBI). The allergens can be allocated to 6 groups according to their sequences (NCBI database) (Wopfner et al, IAAI, 138(4):337-46 (2005)), namely:

Amb a 1/Amb a 2 (95% of patients), pectate lyase family
Amb a 3/Amb a 7 (30-50%; 10-20% respectively), plastocyanins basic prots
Amb a 5 homologues
Amb a 6 (21% of patient), lipid transfer protein
Amb a 8 (35% of patients) profilin
Amb a 9 (10-15% of patients) Ca-binding protein It is widely accepted that the Amb a 1/a 2 group clearly dominates in the population allergic to ragweed. In addition, four variants of Amb a 1 have been described, namely 1.1, 1.2, 1.3 and 1.4 which share high sequence identity. A small proportion of the IgE of the patients exclusively reacted with recombinant Amb a 1.1, whereas the IgE of most patients reacted with Amb a 1.1 as well as Amb a 1.2 and Amb a 1.3 proteins. Another family member of Amb a 1 termed Amb a 1.4 was identified, which appears to be only a minor component of the Amb a 1 family. In addition, Amb a 2 shares 65% identity with Amb a 1 (Wopfner et al, 2005). Since a large majority of the Amb a 1 positive patients react to Amb a 1.1, COPs from that sequence were selected.

Amb a 1 is an acidic (pI 4-6), non-glycosylated single-chain protein with a molecular weight of approximately 38 kDa. It may undergo proteolysis during chromatographic purification and was found to be cleaved into an alpha chain of 26 kDa non-covalently associated with a beta chain of 12 kDa (Wopfner et al, Mol Immunol 46(10):2090-7 (2009)).

The only treatment directed to the cause of IgE-mediated allergy is specific immunotherapy (SIT). The treatment consists in injecting increasing doses of allergens for extended periods of time (three to five years) to induce tolerance in the allergic patient. Several studies showed the benefit of this therapy on the allergic response, in particular upon long-term treatment. (Drachenberg, K. J. et al., Allergol Immunopathol, 31(2):77-82 (2003) and Dam Petersen, K. et al., Allergol Immunopathol 33(5)264-269 (2005)). However, a number of side effects were observed particularly during ultra rush therapies, where up to 30% of the patients have to be treated for allergic symptoms during the course of therapy. (Birnbaum et al., Clin. Exp. Allergy, 33(1):58-64 (2003)). There is thus a strong medical need for an alternative to conventional SIT in the form of a shorter treatment with acceptable safety.

Different approaches have been tested to improve the safety and efficacy of SIT. Formulations or existing extracts have been improved by adding adjuvants, like MPL (Allergy Therapeutics), (Drachenberg, K. J. et al., (2003)) DNA sequences (Hartl, A. et al., Allergy, 59(1):65-73 (2004)) or bacteriophage combined with CpG (Martinez Gomez, J. M. et al., Pharm. Res., 24(10):1927-35 (2007)) which increase the TH1 immune response, thus allowing possible reductions in the amount of allergen extract. Defined allergens were used instead of whole extracts. In the case of birch pollen, a clinical trial with recombinant Bet v 1 has shown efficacy equivalent to whole birch pollen extract (Pauli, G. et al., J. Allergy Clin. Immunol, 122(5):951-60 (2008)). In the case of ragweed, Amb a 1 associated with immunostimulatory DNA sequences appeared to offer long term clinical efficacy on a pilot study (Creticos et al., N Engl J Med, 355:1445-55 (2006)).

To diminish the occurrence of allergic symptoms resulting from treatment, different groups explored the use of products with hypoallergenic potential, namely showing reduced IgE binding. In particular, peptides encompassing a restricted number of T-cell epitopes were used for allergen immunotherapy of cat dander with limited efficacy (Campbell, J D et al., J Exp Med., 206(7):1535-47 (2009)). However, allergens harbor a great variety of T cell epitopes partly dependent on the HLA type of the patient. For example, T cell epitopes were found scattered throughout the Amb a 1 sequence (Jahn-Schmid B. et al., J Allergy Clin Immunol, 126(5):1068-1071 (2010)). Thus an efficient immunotherapy product should preferably contain the complete sequence of the allergen rather than selected T-cell epitopes.

The use of fragments of allergens remains attractive, based on the evidence that human IgE recognize mainly non-contiguous epitopes which may be separated by fragmentation of the allergen. Two contiguous fragments of Bet v 1 or trimeric forms of Bet v 1 were tested in a phase I study in human and showed a trend towards improvement of well being but provided no significant improvement in symptom medication scores (Niederberger, V. et al., Proc Natl Acad Sci USA, 101(2):14677-82 (2004)). In that study, however, a number of adverse events were observed, the majority of which occurred hours after the injections (Purohit, A. et al, Clin Exp Allergy (2008)). Three fragments of the major allergen of bee venom, namely phospholipase A2, were also tested in humans, showing an excellent safety due to lowered IgE binding while eliciting elevated levels of IgG4 and IL-10 (Fellrath et al., J. Allergy Clin. Immunol, 111:854-861 (2003)). A method was devised to select contiguous overlapping peptides (COPs) for treatment of allergy which together form the entire amino acid sequence of an allergen, thus providing all possible T cell epitopes of the allergen, while having lowered IgE binding (U.S. Pat. No. 7,923,209). Such selected fragments show a reduced ability to reform the original tertiary structure of the allergen, if any, resulting in a reduced ability to bind IgE and therefore to elicit allergic reactions in humans.

SUMMARY OF THE INVENTION

According to one aspect, the present invention provides contiguous overlapping peptides (COPs) as a composition for the treatment of ragweed pollen allergies. Specifically, COPs are provided from the sequence of the major allergen of ragweed pollen Amb a 1 which provide all potential T cell epitopes but are devoid of the three dimensional structure of the original allergen, therefore potentially reducing and preferably eliminating their ability to bind IgE. According to one particularly preferred aspect of the invention peptides are provided which are characterized by improved solubility properties compared with other peptides that are insoluble or only slightly soluble in water.

According to a further aspect, the invention relates to a specific immunotherapy (SIT) method able to reduce allergic symptoms after a few administrations over a short period of time. This therapy consists of repeatedly administering specific COPs to humans suffering from ragweed pollen allergy. Administration may be done by systemic, transdermal, intradermal subcutaneous, or by oral routes, or mucosal routes including sublingual and intestinal routes. Administration may in some embodiments be repeated five times over a period of two months compared to 3 to 5 years for current SIT. Administered amounts of active product (COPs) may reach a cumulated value equivalent in molar amount to the amount of Amb a 1 administered over three years of SIT treatment.

Specifically the invention provides a composition comprising a plurality of contiguous overlapping peptide fragments comprising a first peptide consisting of the sequence from amino acids 43-53 to amino acids 96-121 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a second peptide consisting of the sequence from amino acids 96-121 to amino acids 111-147 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a third peptide consisting of the sequence from amino acids 111-147 to amino acids 168-180 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a fourth peptide consisting of the sequence from amino acid 168-190 to amino acids 220-251 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a fifth peptide consisting of the sequence from amino acid 190-241 to amino acids 251-269 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a sixth peptide consisting of the sequence from amino acids 241-269 to amino acids 309-329 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, and a seventh peptide consisting of the sequence from amino acids 309-329 to amino acids 384-396 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

According to an alternative embodiment the composition can comprise only sixpeptide fragments wherein function of the fourth and fifth fragments are performed by a peptide consisting of the sequence from amino acids 168-190 to amino acids 251-269 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

By "eliminating" the reactivity of peptides to IgE antibodies of subject allergic to ragweed pollen is meant providing the absence of clinically significant reaction by the subjects at clinically relevant concentrations of the peptides (such as possible to maintain reactivity with T lymphocytes) as may be evidenced by in vivo tests such as cutaneous tests and/or in vitro tests such as basophil degranulation tests and the like as would be recognized by those of ordinary skill in the art. The present invention is able to provide sets of COPs having $10^{-4}$ and $10^{-5}$ fold lower IgE binding versus binding to the native allergen and such binding levels are consistent with the absence of clinically significant reaction by the allergic subjects.

According to a preferred aspect of the invention, the first and second peptides overlap each other by 1 to 6 amino acids. According to another preferred aspect of the invention the second and third peptides overlap each other by 1 to 10 amino acids. According to another preferred aspect of the invention the third and fourth peptides overlap each other by 1 to 13 amino acids. According to another preferred aspect of the invention the fourth and fifth peptides overlap each other by 1 to 9 amino acids. According to another preferred aspect of the invention the fifth and sixth peptides overlap each other by 1 to 10 amino acids. According to another preferred aspect of the invention the sixth and seventh peptides overlap each other by 1 to 7 amino acids.

Particularly preferred compositions comprise the combination of the peptide having SEQ ID NO: 1, the peptide having SEQ ID NO:2, the peptide having SEQ ID NO: 3, the peptide having SEQ ID NO: 14, the peptide having SEQ ID NO: 15, the peptide having SEQ ID NO: 5, and the peptide having SEQ ID NO: 6

Preferred COP compositions include those wherein the peptides are soluble in aqueous solutions. In particular the set of peptides with SEQ ID NO: 1 to 3, 14, 15 and 5-6 are preferred over peptides with SEQ ID NO 7: to 11

Also provided are peptides having 90% and 80% and 70% or greater sequence identity with the various peptides of SEQ ID NOs: 1-11 and 13-15 and which preferably have reduced or eliminated reactivity to IgE antibodies of patients who are allergic to ragweed pollen which maintaining T lymphocyte reactivity.

Such peptides can be obtained by any of a variety of methods including by chemical synthesis or by recombinant means.

The COPs and peptides of the invention can be provided in dry powdered form but can also be provided in combination with an acceptable carrier or diluent. In addition, the compositions can further comprise an adjuvant with a preferred adjuvant being aluminium hydroxide. As such the compositions can be characterized as and used as a vaccine composition.

Also provided are methods of specific immunotherapy (SIT) against ragweed pollen allergies comprising administering to a patient in need thereof one or more allergens selected from the group consisting of a first peptide consisting of the sequence from amino acids 43-53 to amino acids 96-121 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a second peptide consisting of the sequence from amino acids 96-121 to amino acids 111-147 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a third peptide consisting of the sequence from amino acids 111-147 to amino acid 168-180 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a fourth peptide consisting of the sequence from amino acid 168-190 to amino acids 220-251 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a fifth peptide consisting of the sequence from amino acids 190-241 to amino acids 251-269 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, and a sixth peptide consisting of the sequence from amino acids 241-269 to amino acids 309-329 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, and a seventh peptide consisting of the sequence from amino acids 309-329 to amino acids 384-396 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained. This method may also be practiced wherein the composition comprises only six peptide fragments wherein the fourth and fifth fragments are combined into one peptide consisting of the sequence from amino acids 168-190 to amino acids 251-269 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

Such methods can be carried out in which the peptides are administered using intradermal injection, subcutaneous injection, intramuscular injection, intravenous injection, transdermal, intranasal, oral, sublingual, intraocular, or intrathecal techniques.

According to a preferred aspect of the invention, the first and second peptides overlap each other by 1 to 6 amino acids. According to another preferred aspect of the invention the second and third peptides overlap each other by 1 to 10 amino acids. According to another preferred aspect of the invention the third and fourth peptides overlap each other by 1 to 13 amino acids. According to another preferred aspect of the invention the fourth and fifth peptides overlap each other by 1 to 9 amino acids. According to another preferred aspect of the invention the fifth and sixth peptides overlap each other by 1 to 10 amino acids. According to another preferred aspect of the invention the sixth and seventh peptides overlap each other by 1 to 7 amino acids. According to one preferred aspect of the invention, the patient is treated with at least five of the seven peptides and in another preferred aspect of the invention the patient is treated with at least six of the seven peptides.

BRIEF DESCRIPTION OF THE DRAWINGS

FIG. 5B shows body temperature; and FIG. 5C shows levels of IgE in the sensitized mice.

DETAILED DESCRIPTION OF THE INVENTION

The invention is described below by way of examples with reference to the following experimental procedures and results.

In order to select for products with lowered IgE binding, two sets of long (30-90 amino acids) contiguous overlapping peptides (COP) were devised encompassing the entire Amb a 1 allergen, thus providing all possible T cell epitopes. A first set (A) encompassed six peptides AllerR1, -R2, R3, -R4, -R5 and -R6, with reduced ability to form secondary structures as derived from analysis based on potential IgE epitopes and the tertiary structure of Amb a 1. A second set (Set B) of five COPs, AllerR7, -R8, -R9, -R10 and -R11, was selected. AllerR8 was readily soluble in water, AllerR10 was soluble in aqueous buffer at pH7 but AllerR7, 8, 9 and 11 were only soluble in DMSO but not in water. Due to these unforeseen solubility issues, SetA would be preferred for further development.

In Set A, the only peptide difficult to solubilize in water was AllerR4 (SEQ ID NO:4) although this did not bind IgE as seen in competition ELISA and degranulation assays. Due to difficulties in synthesis and purification, AllerR4 was split in two halves with overlapping ends, called AllerR4.1 (SEQ ID NO:13) and AllerR4.2 (SEQ ID NO:15). Since the split of Amb a 1 in two molecules upon purification does not seem to reflect its natural status within the cell (Wopfner N, et al., (2009)), AllerR4 was prolonged at its N-terminus to overlap with the previous peptide, namely AllerR3. Therefore a third set (C) was selected which contains all peptides included in the Set A except for AllerR4 which is now replaced by AllerR4.3 (SEQ ID 14) and AllerR4.2 (SEQ ID 15). The aim of this change was to provide more soluble peptides than AllerR4 itself as well as to provide the complete natural sequence. The methods of the invention may all be practiced by the substitution of the AllerR4.3 and AllerR4.2 peptides for the AllerR4 peptide.

AllerR4 was purified up to 60% and was only soluble in 50% acetic acid. AllerR4.2, the C-terminal part of AllerR4, showed an improved synthesis and purification was achieved up to 70%. AllerR4.2 was not soluble in H2O, whereas it became soluble at 1 mg/ml after sequential addition of 5 mM HCl (1:4 w/v) and 0.1 M NaOH (1:4.5 v/v to HCl), 0.1 M citrate buffer pH 5.6 (vol. to reach 1 mg/ml). AllerR4.3, the N-terminal part of AllerR4, showed an improved synthesis and purification was achieved up to 60% pure.

The SetA, SetB and SetC of peptides were tested through a combination of in vitro IgE competition tests and Basophil degranulation tests and compared with the original allergen nAmb a 1.

Material and Methods
Allergens
nAmb a 1 was purified from ragweed pollen by Protein Labs (San Diego, Calif.).

Choice of Peptides and Synthesis
The aim was to prevent the formation of stable tertiary structures of B cell epitope, while presenting all T cell epitopes present within the Amb a 1 sequence. As a result, the following COPs which overlap along the Amb -continued SEQ ID NO: 11
GNRFCAPDERSKKNVLGRHGEAAAESMKWNWRTNKDVLENGAIFVASGVDPVLTPEQSAGMIPAEPGES
ALSLTSSAGVLSCQPGA
Molecular weight: 8969.0

Swiss Prot P27759
SEQ ID NO: 12
```
  1 mgikhccyil yftlalvtll qpvrsaedlq eilpvnetrr lttsgaynii dgcwrgkadw
 61 aenrkaladc aqgfgkgtvg gkdgdiytvt selddvanp kegtlrfgaa qnrplwiife
121 rdmvirldke mvvnsdktid grgakveiin agftlngvkn viihninmhd vkvnpgglik
181 sndgpaapra gsdgdaisis gssqiwidhc slsksvdglv daklgttrlt vsnslftqhq
241 fvllfgagde niedrgmlat vafntftdnv dqrmprcrhg ffqvvnnnyd kwgsyaiggs
301 asptilsqgn rfcapdersk knvlgrhgea aaesmkwnwr tnkdvlenga ifvasgvdpv
361 ltpeqsagmi paepgesals ltssagvlsc qpgapc
```

AllerR4.1: aa 190-228 (39 residues)
SEQ ID NO: 13
AGSDGDAISISGSSQIWIDHCSLSKSVDGLVDAKLGTTR
Molecular weight: 3948.33

AllerR4.3: aa 168-228 (60 residues)
SEQ ID NO: 14
MHDVKVNPGGLIKSNDGPAAPRAGSDGDAISISGSSQIWIDHCSLSKSVDGLVDAKLGTTR
Molecular weight: 6203.91

AllerR4.2: aa 220-269 (50 residues)
SEQ ID NO: 15
VDAKLGTTRLTVSNSLFTQHQFVLLFGAGDENIEDRGMLATVAFNTFTDN
Molecular weight: 5477.10

All COPs were synthesized by solid phase fmoc chemistry at research scale to allow determination of IgE binding. Unless otherwise stated, preparative HPLC was used to obtain over 90% pure peptides which were lyophilized. Peptides were resuspended either in water at 2 mg/ml or at 10 to 20 mg per ml in DMSO as indicated and frozen in aliquots.

Competition ELISA

Recombinant Amb a 1 at 0.5 µg/ml (purified nAmb a 1 obtained from Protein Labs, San Diego) was coated overnight on 96-well Nunc Maxisorp® immunoplates (Life Technologies, Basel, Switzerland). After blocking with 1% BSA, either ten-fold, twenty-fold, thirty-fold or forty-fold dilutions of patient serum were added depending on specific IgE content. Biotin Mouse anti-human mAb IgE at 5 µg/ml (PharMingen, BD-Biosciences, San Diego, Calif.) were then added and antibodies were revealed with Streptavidin HRP (PharMingen, BD-Biosciences, San Diego, Calif.) and the substrate TMB (BD Biosciences 10975 Torreyana Rd, San Diego, Calif.). The sera of three allergic patients were selected for high IgE level and clear signal over background and used to test for competition with the peptides. Serial dilutions of each set of COPs, namely Set A; Set B and Set C, at indicted concentrations were pre-incubated with the three selected sera overnight at 4° C. Sera were then incubated on nAmb a 1 coated 96-well plates and residual IgE binding was determined as described above. nAmb a 1 dilutions were used as control for inhibition, whereas BSA was used as control for possible non-specific inhibition.

Basophil Degranulation Tests

BasotestR (ORPEGEN Pharma Heidelberg, Germany) was used for the quantitative determination of in vitro basophile degranulation. Heparinized blood (100 µl) from a non-allergic donor (ACT) was first incubated with serum (25 µl) from a patient allergic to ragweed pollen (FB) for 2 hours. The mix was further stimulated with buffer (reagent B) for 10 min at 37° C., and then with or without chemotactic peptide formylmethionylleucylphenylalanine (fMLP) as positive and negative controls respectively. Aliquots of blood were incubated in parallel with 100 µl allergen solution diluted in a saline solution for 20 min at 37° C. A dose response curve was performed with 250-12.5-0.625-0.031 nano-molar nAmb a 1 (added concentration) as well as starting 10 fold higher with AllerR mixed Sets (AllerR1-R6 and AllerR7-11). The activation process was stopped by incubating the blood samples at 4° C. for 5 min. The samples were then incubated for 20 min at +4° C.) (dark condition with 20 µl of phycoerythrin (PE)-conjugated anti-IgE and fluorescein isothyocyanate (FITC)-conjugated anti-gp53 (CD63). Erythrocytes were subsequently removed by the addition of 2 ml of lysing solution (Becton-Dickinson). Cells were washed twice with PBS solution and resuspended in 200 µl of PBS solution and analyzed within 2 h by flow cytometry (FASC-LSRII-Becton Dickinson). The basophile population was gated on the PE anti-IgE positive cells and the expression of gp53 (CD63) was analyzed on this population. Acquisition was performed on 1,000 cells for each sample and results are given as the percentage of basophils (IgE-positive cells) expressing gp53 (CD63).

Alternatively, degranulation was monitored using Rat Basophilic Leukemia cells (RBL) expressing parts of the human IgE receptor pre-loaded with sera from allergic patients (Vogel et al, Allergy 60: 1021-1028 (2005)). Essentially, RBL-30/25 cells were pre-incubated overnight with sera from patients from the region around Lyon (France, Biomnis) as well as from US (Plasma Lab International). To increase and stabilize the secretion of beta-hexosaminidase, 50% $D_2O$ was added to the Tyrode's buffer used for the assay. beta-hexosaminidase release after IgE crosslinking with an anti-IgE antibody was set to 100% release reflecting the ability of the cells to release beta-hexosaminidase upon IgE crosslinking. Amb a 1-specific release is given as percent of IgE mediated release.

Immunogenicity of AllerR

Amb a 1 and individual COPs were injected i.p. in Balb/c mice. The peptides were given together with an adjuvant, namely Complete Freund's adjuvant or aluminum hydroxide (1 mg/ml Al). Injections were repeated twice at a one month interval with Incomplete Freund's Adjuvant or aluminum hydroxide (1 mg/ml Al). Blood was collected from the retro-orbital sinus 15 days after the last injection and serum prepared by standard method. Results are expressed as arbitrary units (A. U.) corresponding to IgG concentration from which values from pre-immune sera were subtracted.

Anaphylactic Response in Mice

Balb/c mice were sensitized by repeated injections of low doses (1 ug) of the allergen Amb a 1 by 5 subcutaneous injections at 14 days interval. Mice were challenged with high doses of either Amb a 1 (30 μg/animal) or AllerR COPs (40 μg/animal) 7 days after the last injection. Anaphylactic symptoms were scored using a scale of 6 grades (0, no symptoms to 5, death) adapted from Sade et al. J Investig Allergol Clin Immunol; 17(6): 379-385 (2007). Rectal temperature was monitored at 15 minutes intervals for 60 minutes after challenge using a digital thermometer. Citrate buffer was used as control for sensitization and challenge leading to two additional mice groups.

Experimental Results

Choice of Peptides

Amb a 1.1 from *Ambrosia artemisiifolia* is a protein of 396 amino acids (Swiss Prot P27759). The first 25 amino acids have properties of a signal peptide and the mature form consists of amino acids 26-396. Sequencing of the termini of the cleavage products found after purification indicates that the beta subunit start at T43 and ends at K180, whereas the alpha subunit starts at A190 to end at C396 (Wopfner N, et al., (2009))). Two S-S bridges are found, namely C53-C70 and C210-C235. nAmb a 1 is present in different isoforms on the ragweed pollen grains (Swiss Prot P27759, P27760.1, P27761.1, P28744.1) which differ by a few amino acids. In addition the allergen Amb a 2 (P27762.1) shows 65% sequence identity to the Amb a 1 family.

Interestingly, Amb a 1 shows also homology with Jun a 1 (P81294.1) and Cry j 1 (P18632.2), US and Japanese cedar major allergens respectively. All these molecules belong to the Pectate lyase enzyme family. Thus allergenic regions might be found in equivalent locations on the three dimensional structure of the molecules allowing the ability to further predict where to set the ends of the COPs.

Description of B cell epitopes or IgE epitopes is rather scarce in the literature. Recombinant Amb a 1 required reduction and heat treatment to react with IgE from allergic patients (Wopfner N, et al., (2009))). Interpretation included possible refolding on nitrocellulose. Alternatively, linear epitopes may have been present which were masked by improper folding in E coli.

A number of monoclonal antibodies were generated against nAmb a 1 or its recombinant form (Wopfner et al, Clin and Exp Allergy, 38, 219-226 (2007))). Even though Amb a 1 alpha subunit (aa 181-396) showed a slightly lower IgE reactivity than the beta proteolytic product, no epitope mapping was performed. Two allergenic sites were identified by using monoclonal antibodies on ragweed pollen allergen antigen E (Amb a 1 at the time) (Olson J R, Klapper D G J Immunol 1986; 136:2109-15) but no exact mapping was performed.

Potential epitopes can be predicted using epitope computer predictive tools as proposed in the Immune epitope and database and analysis resource (IEDB) (http://immuneepitope.org/). In particular, ElliPro predicts linear and discontinuous antibody epitopes based on a protein antigen's three dimensional structure. Combining knowledge about the mature protein missing the first residues, the prediction of potential linear epitopes as well as the prediction of discontinuous epitopes, two sets of COPs were proposed as presented in SEQ ID Nos. 1 to 11.

IgE Binding of Selected COPs Compared to nAmb a 1

COPs sets A and B were first tested in vitro for reduced IgE binding by competition ELISA as described previously in material and methods. As seen in FIG. 1, nAmb a 1 competed with IgE present in the sera at concentrations ranging from $10^{-11}$ to $10^{-8}$ M, whereas BSA showed no detectable inhibition at all concentrations tested. Both SetA and SetB showed no competition. Competition assays were performed with sera from three allergic patients (17794, 18342 and FB), confirming the absence of competition of the combined sets with Amb a 1 for IgE binding (FIG. 1, panels A, B and C, respectively).

Human Basophil Degranulation Tests

In order to further verify the absence of IgE binding in a test closer to the human body, the COPs were tested in a basophil degranulation assay (Basotest®). Human basophils, loaded with human serum FB, degranulated when stimulated with nAmb a 1 in a concentration dependent manner (FIG. 2). On the contrary, combinations of COPs (AllerR1 to AllerR6 and AllerR7 to R11) were unable to induce degranulation above the level observed with a negative control. No degranulation was observed through a range of COPs concentrations up to 1,000 fold that of the Amb a 1 concentration able to induce half maximal degranulation (FIG. 2). The absence of degranulation of basophils indicates a potentially diminished risk of immediate allergic reaction upon application in human.

From these experiments it can be concluded that a preferred product to be called AllerR will contain a combination of soluble peptides as present in Set A, namely a combination of the six peptides AllerR1, -R2, -R3, -R4, -R5 and -R6. Set A represents a better candidate for the treatment of ragweed pollen allergy than Set B, namely the combination of AllerR7, -R8, -R9, -R10 and -R11, since three out of five of the later peptides had to be dissolved in DMSO, indicating solubility difficulties as shown in Table I.

TABLE I

Solubility Characteristics of COPs

| COP | MW | Solvent | Conc. |
|---|---|---|---|
| Set A | | | |
| AllerR1 | 6223 | $H_2O$ | 2 mg/ml |
| AllerR2 | 5901 | $H_2O$ | 2 mg/ml |
| AllerR3 | 4581 | $H_2O$ | 2 mg/ml |
| AllerR4 | 8465 | DMSO | 10 mg/ml |
| AllerR4.3 | 6204 | $H_2O$ | 2 mg/ml |
| AllerR4.2 | 5477 | $H_2O$, after sequential addition of 5 mM HC1 (1:4 w/v), 0.1M NaOH (1:4.5 v/v to HC1) and 0.1M citrate buffer pH 5.6 | 1 mg/ml |
| AllerR5 | 7864 | $H_2O$ | 2 mg/ml |
| AllerR6 | 7365 | DMSO | 1 mg/ml |
| Set B | | | |
| AllerR7 | 8580 | DMSO | 1 mg/ml |
| AllerR8 | 7909 | $H_2O$ | 8 mg/ml |
| AllerR9 | 6468 | DMSO | 20 mg/ml |
| AllerR10 | 8795 | $H_2O$, in aqueous buffer pH 7 | 2 mg/ml |
| AllerR11 | 8969 | DMSO | 20 mg/ml |

Improved Composition

A further improvement of the invention includes splitting the AllerR4 peptide in two COPs, namely AllerR4.3 and AllerR4.2, with improved purification and solubility properties. AllerR4.3 not only includes the N-terminal part of AllerR4, but also was extended to overlap with AllerR3 and therefore encompass all natural sequences. Indeed, natural Amb a 1 seems to be split in two halves upon purification only.

The improved composition AllerR composed of the seven COPs, namely AllerR1, 2, 4.3, 4.2, 5 and 6, was tested in competition ELISA tests using a panel of sera from patients allergic to ragweed. Sera from 22 patients were pre-incubated with increasing concentrations of either nAmb a 1 or AllerR (data not shown). All sera showed competition in the range of $10^{-11}$ to $10^{-8}$ molar nAmb a 1, whereas none reacted with AllerR, up to $10^{-5}$ M, confirming lack of detectable IgE binding to any of the COPs composing the product.

Figure 1:
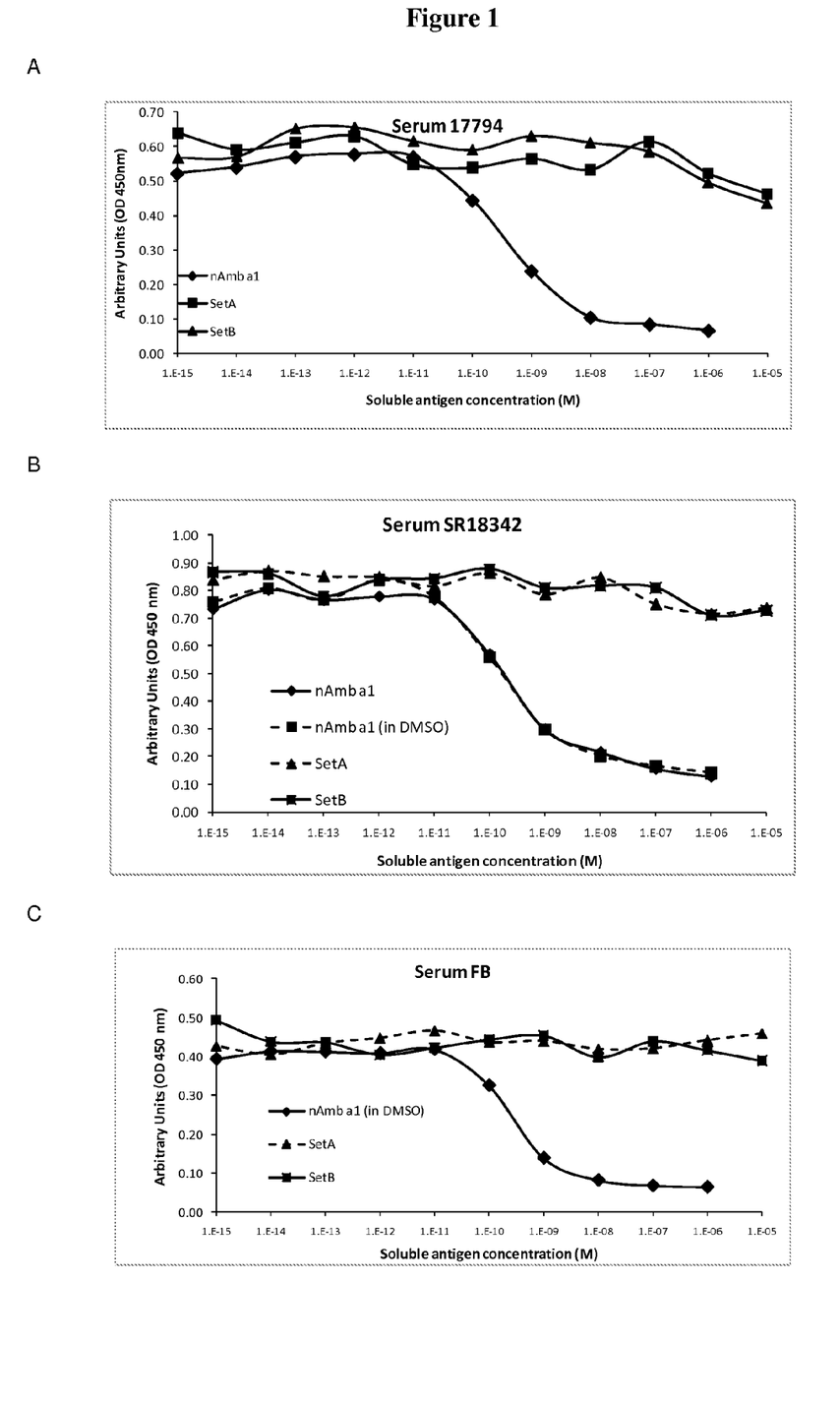
FIG. 1 depicts the competitive binding of selected COPs to IgE compared to Amb a 1. COPs were mixed in equimolar amounts as SetA (AllerR1 to AllerR6) or SetB (AllerR7 to AllerR11) and pre-incubated at indicated concentrations with serum from three subjects allergic to ragweed pollen (No 17794, 18342 and FB in panels A, B and C respectively). Residual Amb a 1 specific IgE was monitored using ELISA plates coated with nAmb a 1. nAmb a 1 is used as positive control.
Figure 2:
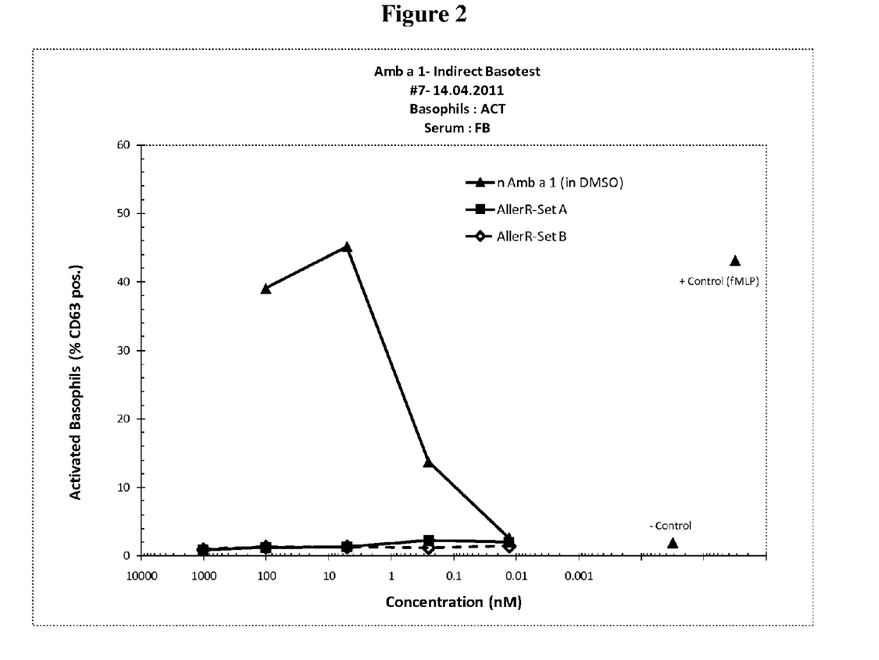
FIG. 2 depicts the ability of nAmb a 1 to induce human basophil degranulation in a Basotest® assay. Combined COPs in Sets A or B do not induce basophil degranulation at any tested concentration.
Figure 3:
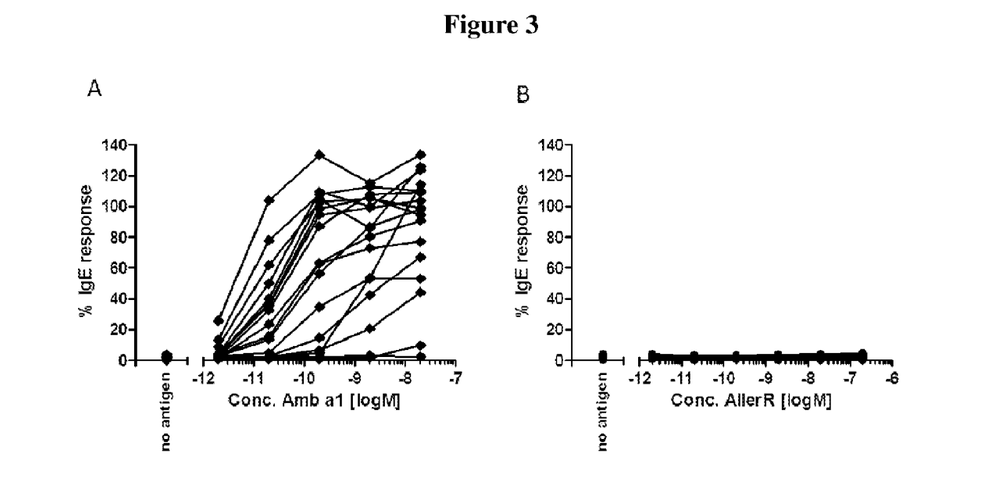
FIG. 3 depicts the non-reactivity of AllerR with IgE from a panel of allergic subjects using a Rat basophil cells degranulation. RBL cells expressing human IgE receptor were pre-incubated with sera from a panel of allergic patients span. Control nAmb a 1 triggered degranulation to various extents (FIG. 3, panel A). AllerR does not induce degranulation with any of the 21 sera tested (FIG. 3, panel B).

AllerR was further tested for basophil degranulation. RBL cells expressing human IgE receptor were pre-incubated with sera from the same panel of allergic patients. Control nAmb a 1 triggered degranulation to various extend, probably reflecting variability in either IgE level or affinity (FIG. 3, panel A). AllerR did not induce degranulation with any of the 21 sera tested (FIG. 3, panel B). Thus AllerR shows no detectable IgE binding under the conditions tested. In summary, IgE binding capacity of AllerR is at least a 100,000 fold less than that of Amb a 1 both in competition ELISA and degranulation tests.

Immunisation

Figure 4:
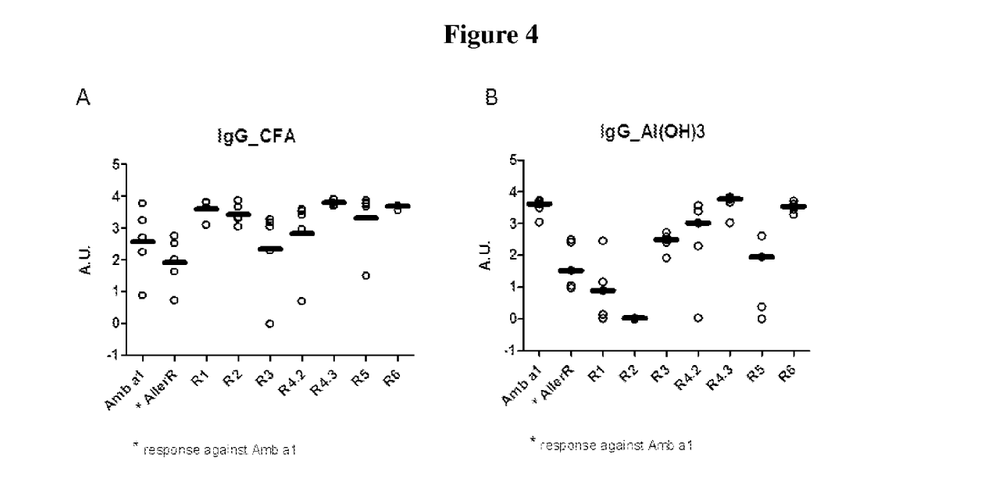
FIG. 4 depicts the immunogenicity of Aller R and each of its COPs. AllerR mix and individual COPs were injected in Balb/c mice with Freund adjuvant (panel A) or Aluminum hydroxide (panel B) as adjuvant. Measured IgG levels after intraperitoneal injection indicate that each peptide AllerR1 to AllerR6 is able to elicit an IgG response. Furthermore, the IgG raised by the AllerR mix recognize natural Amb a 1 (FIG. 4 panel A).

Aller R and each separate COP individually were injected in Balb/c mice with Freund adjuvant. IgG levels were measured after intraperitoneal injection (FIG. 4). Each peptide AllerR1 to AllerR6 is able to elicit an IgG response and therefore contributes to the immune response against the AllerR mix. IgG raised by the AllerR mix recognizes natural Amb a 1 (FIG. 4 panel A). In separate experiments, the presence of IgGs against each individual COP can be detected in sera from mice immunized with AllerR. Furthermore, sera from mice immunized with single peptides can be tested for the presence of Amb a 1 specific IgG. Such results will show that AllerR can induce an immune response in mice against nAmb a 1 and that each of the seven COPs within AllerR can contribute to immunogenicity.

Immunogenicity was also observed using aluminum hydroxide instead of Freund adjuvant, albeit leading to more variable IgG levels against Amb a 1 (FIG. 4, panel B)

Sensitization and Challenge

Figure 5:
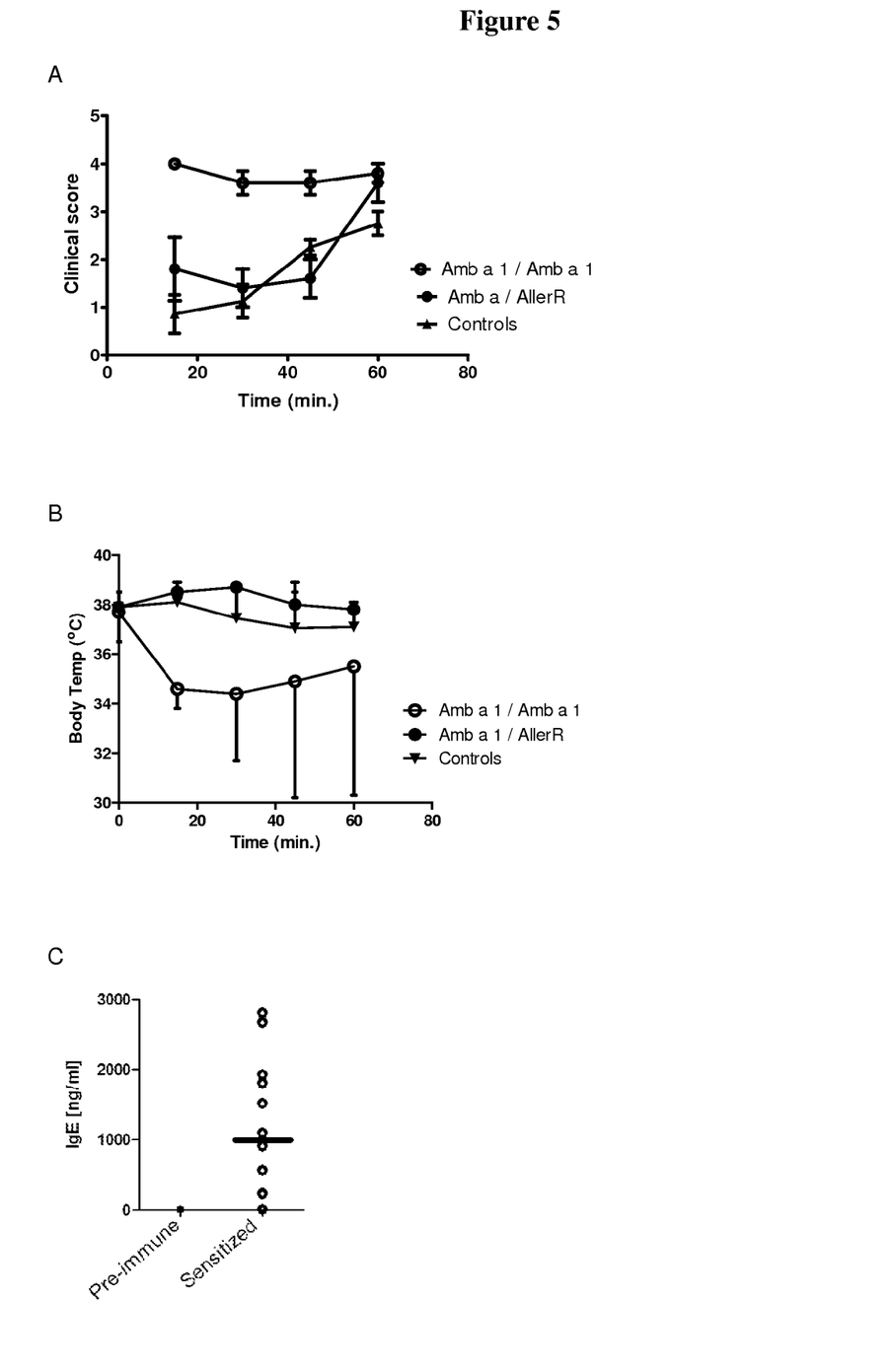
FIG. 5 depicts the anaphylactic reactions of Balb/c mice sensitized by repeated subcutaneous injections of nAmb a 1.7 days after the fifth injection of low dose of nAmb a 1 mice were challenged with a single massive dose of allergen. Panel A shows anaphylactic symptoms scored according to a pre-defined scale ranging from 0 (no symptom) to 5 (death of the animal)

Balb/c mice were sensitized by repeated subcutaneous injections of nAmb a 1 (1 µg/ml. 7 days after the last injection mice were challenged with a single massive dose of allergen (Amb a 1 at 30 µg/ml) or AllerR (34 µg/ml. Mice were observed for one hour and anaphylactic symptoms scored according to a predefined scale ranging from 0 (no symptom) to 5 (death of the animal). Control mice either non-sensitized (citrate buffer injected only) or sensitized with Amb a 1 and challenged with citrate buffer only showed low symptom scores and were pooled (FIG. 5, panel A, controls). The increase in symptom scores observed after one hour results probably from the stress of the animals being sampled for rectal temperature. AllerR showed essentially identical symptoms to controls whereas challenge with Amb a 1 resulted in a significant increase in symptom scores already after 15 min. Thus AllerR does not trigger an anaphylactic shock in Amb a 1 sensitized mice.

In parallel, body temperature was measured every 15 min (FIG. 5, panel B). Controls and AllerR challenges resulted in essentially no temperature drop, whereas Amb a 1 induced a marked decrease in rectal temperature. The presence of increased levels of IgE was measured in sensitized mice (FIG. 5, panel C). IgE mean levels were increased by about 500 fold over pre-immune following sensitization. These results show that AllerR differs from Amb a 1 by its lack of challenging activity, indicating that AllerR does not interact with immunoglobulins (probably IgE) raised by Amb a 1 during sensitization.

Variations in the Invention

Also contemplated are homologs of the AllerR1 to R6 COPs, by amino acid changes within each peptide to produce homologs thereof wherein the reactivity of the homologs to IgE antibodies of patients who are allergic to ragweed pollen is eliminated while that with the T lymphocytes is still retained. Further contemplated are homologs of the COPs by shifting the limits of the COPs within the ragweed pollen major allergen Amb a 1. Such homologs will result in products with equivalent profiles of non detectable IgE binding and T lymphocyte activity. Such products will present the same potential for safety and efficacy in human as AllerR and can be considered as equivalent in terms of chances for treatment, unless shown otherwise. Suitable homologs characterized by no reactivity to anti ragweed pollen IgE antibodies while maintaining reactivity to T lymphocytes may be identified by the methods described herein. Also contemplated are sets of COPs with reduced or eliminated IgE reactivity which retain T lymphocyte reactivity but which are also soluble and/or which show improved synthesis and purification.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A composition comprising a plurality of peptide fragments comprising a first polypeptide consisting of the sequence from amino acids 43-53 to amino acids 96-121 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a second peptide consisting of the sequence from amino acids 96-121 to amino acids 111-147 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a third peptide consisting of the sequence from amino acids 111-147 to amino acid 168-180 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a fourth peptide consisting of the sequence from amino acid 168-190 to amino acids 220-251 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a fifth peptide consisting of the sequence from amino acids 190-241 to amino acids 251-269 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a sixth peptide consisting of the sequence from amino acids 241-269 to amino acids 309-329 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained and a seventh peptide consisting of the sequence from amino acids 309-329 to amino acids 384-396 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

2. The composition of claim 1 wherein the first and second peptides overlap each other by 1 to 6 amino acids.

3. The composition of claim 1 wherein the second and third peptides overlap each other by 1 to 10 amino acids.

4. The composition of claim 1 wherein the third and fourth peptides overlap each other by 1 to 13 amino acids.

5. The composition of claim 1 wherein the fourth and fifth peptides overlap each other by 1 to 9 amino acids.

6. The composition of claim 1 wherein the fifth and sixth peptides overlap each other by 1 to 10 peptides.

7. The composition of claim 1 wherein the sixth and seventh peptides overlap each other by 1 to 7 peptides.

8. A composition comprising a plurality of peptide fragments comprising a first polypeptide consisting of the sequence from amino acids 43-53 to amino acids 96-121 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a second peptide consisting of the sequence from amino acids 96-121 to amino acids 111-147 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a third peptide consisting of the sequence from amino acids 111-147 to amino acid 168-180 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a fourth peptide consisting of the sequence from amino acid 168-190 to amino acids 251-269 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained, a fifth peptide consisting of the sequence from amino acids 241-269 to amino acids 309-329 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained and a sixth peptide consisting of the sequence from amino acids 309-329 to amino acids 384-396 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

9. The composition of claim 8 wherein the first and second peptides overlap each other by 1 to 6 amino acids.

10. The composition of claim 8 wherein the second and third peptides overlap each other by 1 to 10 amino acids.

11. The composition of claim 8 wherein the third and fourth peptides overlap each other by 1 to 12 amino acids.

12. The composition of claim 8 wherein the fourth and fifth peptides overlap each other by 1 to 10 peptides.

13. The composition of claim 8 wherein the fifth and sixth peptides overlap each other by 1 to 7 peptides.

14. The composition of claim 1 wherein the first peptide is SEQ ID NO: 1; wherein the second peptide is SEQ ID NO: 2; wherein the third peptide is SEQ ID NO: 3; wherein the fourth peptide is SEQ ID NO: 14; wherein the fifth peptide is SEQ ID NO: 15; wherein the sixth peptide is SEQ ID NO: 5; and wherein the seventh peptide is SEQ ID NO: 6.

15. The composition of claim 8 wherein the first peptide is SEQ ID NO: 1; wherein the second peptide is SEQ ID NO: 2; wherein the third peptide is SEQ ID NO: 3; wherein the fourth peptide is SEQ ID NO: 4; wherein the fifth peptide is SEQ ID NO: 5; and wherein the sixth peptide is SEQ ID NO: 6.

16. A composition comprising a combination of the peptides consisting of SEQ ID NO: 7; SEQ ID NO: 8; SEQ ID NO: 9; SEQ ID NO 10; and SEQ ID NO: 11.

17. A peptide consisting of the sequence of SEQ ID NO: 1.

18. A peptide consisting of the sequence SEQ ID NO 7.

19. A peptide consisting of the sequence of SEQ ID NO: 2.

20. A peptide consisting of the sequence from amino acids 111-147 to amino acid 168-180 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

21. The peptide of claim 20 which has the sequence of SEQ ID NO: 3.

22. The peptide of claim 20 which has the sequence SEQ ID NO 8.

23. A peptide consisting of the sequence from amino acids 168-190 to amino acid 220-251 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

24. The peptide of claim 23 which has the sequence of SEQ ID NO: 13.

25. The peptide of claim 23 which has the sequence of SEQ ID NO: 14.

26. A peptide consisting of the sequence SEQ ID NO 15.

27. A peptide consisting of the sequence from amino acids 241-269 to amino acid 309-329 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

28. The peptide of claim 27 which has the sequence of SEQ ID NO: 5.

29. The peptide of claim 27 which has the sequence SEQ ID NO 10.

30. A peptide consisting of the sequence from amino acids 309-329 to amino acid 384-396 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained.

31. The peptide of claim 30 which has the sequence of SEQ ID NO: 6.

32. The peptide of claim 30 which has the sequence SEQ ID NO 11.

33. The composition of claim 1 which is provided in dry powdered form.

34. The composition of claim 1 further comprising a pharmaceutically acceptable carrier or diluent.

35. The composition of claim 34 further comprising an adjuvant.

36. The composition of claim 35 wherein the adjuvant is aluminium hydroxide.

37. A method of specific immunotherapy against ragweed pollen allergies comprising administering to a patient in need thereof at least five allergens selected from the group consisting of
- a first peptide consisting of the sequence from amino acids 43-53 to amino acids 96-121 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained,
- a second peptide consisting of the sequence from amino acids 96-121 to amino acids 111-147 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained,
- a third peptide consisting of the sequence from amino acids 111-147 to amino acid 168-180 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained,
- a fourth peptide consisting of the sequence from amino acid 168-190 to amino acids 220-251 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained,
- a fifth peptide consisting of the sequence from amino acids 190-241 to amino acids 251-269 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained,
- a sixth peptide consisting of the sequence from amino acids 241-269 to amino acids 309-329 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained and
- a seventh peptide consisting of the sequence from amino acids 309-329 to amino acids 384-396 of SEQ ID NO: 12 wherein the reactivity of said peptide to IgE antibodies of subjects who are allergic to ragweed pollen is eliminated while the reactivity with the T lymphocytes from subjects who are allergic to ragweed pollen is retained wherein said allergens are administered in a dosage that stimulates a T cell response without stimulating an IgE response.

38. The method of claim 37 wherein the peptides are administered using intradermal injection, subcutaneous injection, intramuscular injection, intravenous injection, transdermal, intranasal, oral, sublingual, intraocular, or intrathecal techniques.

39. The method of claim 37 wherein the patient is treated with at least six of said seven peptides.

* * * * *

UNITED STATES PATENT AND TRADEMARK OFFICE
CERTIFICATE OF CORRECTION

PATENT NO.         : 9,005,627 B2
APPLICATION NO.    : 13/533656
DATED              : April 14, 2015
INVENTOR(S)        : Christophe Reymond et al.

Page 1 of 1

It is certified that error appears in the above-identified patent and that said Letters Patent is hereby corrected as shown below:

In the Specification:

At Column 2, line 16, "ultra rush" should be -- ultra-rush --.

At Column 2, line 57, "well being" should be -- well-being --.

At Column 4, line 13, "sixpeptide" should be -- six peptide --.

At Column 14, line 28, "non detectable" should be -- non-detectable --.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 15

<210> SEQ ID NO 1
<211> LENGTH: 59
<212> TYPE: PRT
<213> ORGANISM: Artificial Sequence
<220> FEATURE:
<223> OTHER INFORMATION: Synthetic peptide

<400> SEQUENCE: 1

Thr Ser Gly Ala Tyr Asn Ile Ile Asp Gly Cys Trp Arg Gly Lys Ala
1               5                   10                  15

Asp Trp Ala Glu Asn Arg Lys Ala Leu Ala Asp Cys Ala Gln Gly Phe
            20                  25                  30

Gly Lys Gly Thr Val Gly Gly Lys Asp Gly Asp Ile Tyr Thr Val Thr
        35                  40                  45

Ser Glu Leu Asp Asp Asp Val Ala Asn Pro Lys
    50                  55

<210> SEQ ID NO 2
<211> LENGTH: 52
<212> TYPE: PRT
<213> ORGANISM: Artificial Sequence
<220> FEATURE:
<223> OTHER INFORMATION: Synthetic peptide

<400> SEQUENCE: 2

Asp Val Ala Asn Pro Lys Glu Gly Thr Leu Arg Phe Gly Ala Ala Gln
1               5                   10                  15

Asn Arg Pro Leu Trp Ile Ile Phe Glu Arg Asp Met Val Ile Arg Leu
            20                  25                  30

Asp Lys Glu Met Val Val Asn Ser Asp Lys Thr Ile Asp Gly Arg Gly
        35                  40                  45

Ala Lys Val Glu
    50

<210> SEQ ID NO 3
<211> LENGTH: 43
<212> TYPE: PRT
<213> ORGANISM: Artificial Sequence
<220> FEATURE:
<223> OTHER INFORMATION: Synthetic peptide

<400> SEQUENCE: 3

Thr Ile Asp Gly Arg Gly Ala Lys Val Glu Ile Ile Asn Ala Gly Phe
1               5                   10                  15

Thr Leu Asn Gly Val Lys Asn Val Ile Ile His Asn Ile Asn Met His
            20                  25                  30

Asp Val Lys Val Asn Pro Gly Gly Leu Ile Lys
        35                  40

<210> SEQ ID NO 4
<211> LENGTH: 80
<212> TYPE: PRT
<213> ORGANISM: Artificial Sequence
<220> FEATURE:
<223> OTHER INFORMATION: Synthetic peptide

<400> SEQUENCE: 4

Ala Gly Ser Asp Gly Asp Ala Ile Ser Ile Ser Gly Ser Ser Gln Ile
1               5                   10                  15

Trp Ile Asp His Cys Ser Leu Ser Lys Ser Val Asp Gly Leu Val Asp
            20                  25                  30

Ala Lys Leu Gly Thr Thr Arg Leu Thr Val Ser Asn Ser Leu Phe Thr
        35                  40                  45

Gln His Gln Phe Val Leu Leu Phe Gly Ala Gly Asp Glu Asn Ile Glu
    50                  55                  60

Asp Arg Gly Met Leu Ala Thr Val Ala Phe Asn Thr Phe Thr Asp Asn
65                  70                  75                  80

<210> SEQ ID NO 5
<211> LENGTH: 70
<212> TYPE: PRT
<213> ORGANISM: Artificial Sequence
<220> FEATURE:
<223> OTHER INFORMATION: Synthetic peptide

<400> SEQUENCE: 5

Thr Val Ala Phe Asn Thr Phe Thr Asp Asn Val Asp Gln Arg Met Pro
1               5                   10                  15

Arg Cys Arg His Gly Phe Phe Gln Val Val Asn Asn Asn Tyr Asp Lys
            20                  25                  30

Trp Gly Ser Tyr Ala Ile Gly Gly Ser Ala Ser Pro Thr Ile Leu Ser
            35                  40                  45

Gln Gly Asn Arg Phe Cys Ala Pro Asp Glu Arg Ser Lys Lys Asn Val
50                      55                  60

Leu Gly Arg His Gly Glu
65                  70

<210> SEQ ID NO 6
<211> LENGTH: 72
<212> TYPE: PRT
<213> ORGANISM: Artificial Sequence
<220> FEATURE:
<223> OTHER INFORMATION: Synthetic peptide

<400> SEQUENCE: 6

Val Leu Gly Arg His Gly Glu Ala Ala Ala Glu Ser Met Lys Trp Asn
1               5                   10                  15

Trp Arg Thr Asn Lys Asp Val Leu Glu Asn Gly Ala Ile Phe Val Ala
            20                  25                  30

Ser Gly Val Asp Pro Val Leu Thr Pro Glu Gln Ser Ala Gly Met Ile
            35                  40                  45

Pro Ala Glu Pro Gly Glu Ser Ala Leu Ser Leu Thr Ser Ser Ala Gly
50                      55                  60

Val Leu Ser Cys Gln Pro Gly Ala
65                  70

<210> SEQ ID NO 7
<211> LENGTH: 79
<212> TYPE: PRT
<213> ORGANISM: Artificial Sequence
<220> FEATURE:
<223> OTHER INFORMATION: Synthetic peptide

<400> SEQUENCE: 7

Thr Ser Gly Ala Tyr Asn Ile Ile Asp Gly Cys Trp Arg Gly Lys Ala
1               5                   10                  15

Asp Trp Ala Glu Asn Arg Lys Ala Leu Ala Asp Cys Ala Gln Gly Phe
            20                  25                  30

Gly Lys Gly Thr Val Gly Gly Lys Asp Gly Asp Ile Tyr Thr Val Thr
            35                  40                  45

Ser Glu Leu Asp Asp Asp Val Ala Asn Pro Lys Glu Gly Thr Leu Arg
50                      55                  60

Phe Gly Ala Ala Gln Asn Arg Pro Leu Trp Ile Ile Phe Glu Arg
65                  70                  75

<210> SEQ ID NO 8
<211> LENGTH: 70
<212> TYPE: PRT
<213> ORGANISM: Artificial Sequence
<220> FEATURE:
<223> OTHER INFORMATION: Synthetic peptide

<400> SEQUENCE: 8

Gln Asn Arg Pro Leu Trp Ile Ile Phe Glu Arg Asp Met Val Ile Arg
1               5                   10                  15

Leu Asp Lys Glu Met Val Val Asn Ser Asp Lys Thr Ile Asp Gly Arg
            20                  25                  30

```
Gly Ala Lys Val Glu Ile Ile Asn Ala Gly Phe Thr Leu Asn Gly Val
         35                  40                  45

Lys Asn Val Ile Ile His Asn Ile Asn Met His Asp Val Lys Val Asn
 50                  55                  60

Pro Gly Gly Leu Ile Lys
 65                  70

<210> SEQ ID NO 9
<211> LENGTH: 62
<212> TYPE: PRT
<213> ORGANISM: Artificial Sequence
<220> FEATURE:
<223> OTHER INFORMATION: Synthetic peptide

<400> SEQUENCE: 9

Ala Gly Ser Asp Gly Asp Ala Ile Ser Ile Ser Gly Ser Ser Gln Ile
 1               5                   10                  15

Trp Ile Asp His Cys Ser Leu Ser Lys Ser Val Asp Gly Leu Val Asp
                 20                  25                  30

Ala Lys Leu Gly Thr Thr Arg Leu Thr Val Ser Asn Ser Leu Phe Thr
             35                  40                  45

Gln His Gln Phe Val Leu Phe Gly Ala Gly Asp Glu Asn
         50                  55                  60

<210> SEQ ID NO 10
<211> LENGTH: 79
<212> TYPE: PRT
<213> ORGANISM: Artificial Sequence
<220> FEATURE:
<223> OTHER INFORMATION: Synthetic peptide

<400> SEQUENCE: 10

Phe Val Leu Leu Phe Gly Ala Gly Asp Glu Asn Ile Glu Asp Arg Gly
 1               5                   10                  15

Met Leu Ala Thr Val Ala Phe Asn Thr Phe Thr Asp Asn Val Asp Gln
                 20                  25                  30

Arg Met Pro Arg Cys Arg His Gly Phe Phe Gln Val Val Asn Asn Asn
             35                  40                  45

Tyr Asp Lys Trp Gly Ser Tyr Ala Ile Gly Gly Ser Ala Ser Pro Thr
         50                  55                  60

Ile Leu Ser Gln Gly Asn Arg Phe Cys Ala Pro Asp Glu Arg Ser
 65                  70                  75

<210> SEQ ID NO 11
<211> LENGTH: 86
<212> TYPE: PRT
<213> ORGANISM: Artificial Sequence
<220> FEATURE:
<223> OTHER INFORMATION: Synthetic peptide

<400> SEQUENCE: 11

Gly Asn Arg Phe Cys Ala Pro Asp Glu Arg Ser Lys Lys Asn Val Leu
 1               5                   10                  15

Gly Arg His Gly Glu Ala Ala Ala Glu Ser Met Lys Trp Asn Trp Arg
                 20                  25                  30

Thr Asn Lys Asp Val Leu Glu Asn Gly Ala Ile Phe Val Ala Ser Gly
             35                  40                  45

Val Asp Pro Val Leu Thr Pro Glu Gln Ser Ala Gly Met Ile Pro Ala
         50                  55                  60

Glu Pro Gly Glu Ser Ala Leu Ser Leu Thr Ser Ser Ala Gly Val Leu
```

Ser Cys Gln Pro Gly Ala
            85

<210> SEQ ID NO 12
<211> LENGTH: 396
<212> TYPE: PRT
<213> ORGANISM: Artificial Sequence
<220> FEATURE:
<223> OTHER INFORMATION: Synthetic peptide

<400> SEQUENCE: 12

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
            20                  25                  30

Leu Pro Val Asn Glu Thr Arg Arg Leu Thr Thr Ser Gly Ala Tyr Asn
        35                  40                  45

Ile Ile Asp Gly Cys Trp Arg Gly Lys Ala Asp Trp Ala Glu Asn Arg
    50                  55                  60

Lys Ala Leu Ala Asp Cys Ala Gln Gly Phe Gly Lys Gly Thr Val Gly
65                  70                  75                  80

Gly Lys Asp Gly Asp Ile Tyr Thr Val Thr Ser Glu Leu Asp Asp Asp
                85                  90                  95

Val Ala Asn Pro Lys Glu Gly Thr Leu Arg Phe Gly Ala Ala Gln Asn
            100                 105                 110

Arg Pro Leu Trp Ile Ile Phe Glu Arg Asp Met Val Ile Arg Leu Asp
        115                 120                 125

Lys Glu Met Val Val Asn Ser Asp Lys Thr Ile Asp Gly Arg Gly Ala
    130                 135                 140

Lys Val Glu Ile Ile Asn Ala Gly Phe Thr Leu Asn Gly Val Lys Asn
145                 150                 155                 160

Val Ile Ile His Asn Ile Asn Met His Asp Val Lys Val Asn Pro Gly
                165                 170                 175

Gly Leu Ile Lys Ser Asn Asp Gly Pro Ala Ala Pro Arg Ala Gly Ser
            180                 185                 190

Asp Gly Asp Ala Ile Ser Ile Ser Gly Ser Ser Gln Ile Trp Ile Asp
        195                 200                 205

His Cys Ser Leu Ser Lys Ser Val Asp Gly Leu Val Asp Ala Lys Leu
    210                 215                 220

Gly Thr Thr Arg Leu Thr Val Ser Asn Ser Leu Phe Thr Gln His Gln
225                 230                 235                 240

Phe Val Leu Leu Phe Gly Ala Gly Asp Glu Asn Ile Glu Asp Arg Gly
                245                 250                 255

Met Leu Ala Thr Val Ala Phe Asn Thr Phe Thr Asp Asn Val Asp Gln
            260                 265                 270

Arg Met Pro Arg Cys Arg His Gly Phe Phe Gln Val Val Asn Asn Asn
        275                 280                 285

Tyr Asp Lys Trp Gly Ser Tyr Ala Ile Gly Gly Ser Ala Ser Pro Thr
    290                 295                 300

Ile Leu Ser Gln Gly Asn Arg Phe Cys Ala Pro Asp Glu Arg Ser Lys
305                 310                 315                 320

Lys Asn Val Leu Gly Arg His Gly Glu Ala Ala Glu Ser Met Lys
                325                 330                 335

Trp Asn Trp Arg Thr Asn Lys Asp Val Leu Glu Asn Gly Ala Ile Phe

```
                    340              345              350
Val Ala Ser Gly Val Asp Pro Val Leu Thr Pro Glu Gln Ser Ala Gly
                355              360              365

Met Ile Pro Ala Glu Pro Gly Glu Ser Ala Leu Ser Leu Thr Ser Ser
    370              375              380

Ala Gly Val Leu Ser Cys Gln Pro Gly Ala Pro Cys
385              390              395

<210> SEQ ID NO 13
<211> LENGTH: 39
<212> TYPE: PRT
<213> ORGANISM: Artificial Sequence
<220> FEATURE:
<223> OTHER INFORMATION: Synthetic peptide

<400> SEQUENCE: 13

Ala Gly Ser Asp Gly Asp Ala Ile Ser Ile Ser Gly Ser Ser Gln Ile
1               5                   10                  15

Trp Ile Asp His Cys Ser Leu Ser Lys Ser Val Asp Gly Leu Val Asp
            20                  25                  30

Ala Lys Leu Gly Thr Thr Arg
        35

<210> SEQ ID NO 14
<211> LENGTH: 61
<212> TYPE: PRT
<213> ORGANISM: Artificial Sequence
<220> FEATURE:
<223> OTHER INFORMATION: Synthetic peptide

<400> SEQUENCE: 14

Met His Asp Val Lys Val Asn Pro Gly Gly Leu Ile Lys Ser Asn Asp
1               5                   10                  15

Gly Pro Ala Ala Pro Arg Ala Gly Ser Asp Gly Asp Ala Ile Ser Ile
            20                  25                  30

Ser Gly Ser Ser Gln Ile Trp Ile Asp His Cys Ser Leu Ser Lys Ser
        35                  40                  45

Val Asp Gly Leu Val Asp Ala Lys Leu Gly Thr Thr Arg
    50                  55                  60

<210> SEQ ID NO 15
<211> LENGTH: 50
<212> TYPE: PRT
<213> ORGANISM: Artificial Sequence
<220> FEATURE:
<223> OTHER INFORMATION: Synthetic peptide

<400> SEQUENCE: 15

Val Asp Ala Lys Leu Gly Thr Thr Arg Leu Thr Val Ser Asn Ser Leu
1               5                   10                  15

Phe Thr Gln His Gln Phe Val Leu Leu Phe Gly Ala Gly Asp Glu Asn
            20                  25                  30

Ile Glu Asp Arg Gly Met Leu Ala Thr Val Ala Phe Asn Thr Phe Thr
        35                  40                  45

Asp Asn
    50
```